(12) United States Patent
Hoffman

(10) Patent No.: US 9,687,528 B2
(45) Date of Patent: Jun. 27, 2017

(54) TRANSDERMAL FORMULATIONS

(71) Applicant: Steven Hoffman, Mahway, NJ (US)

(72) Inventor: Steven Hoffman, Mahway, NJ (US)

( * ) Notice: Subject to any disclaimer, the term of this patent is extended or adjusted under 35 U.S.C. 154(b) by 0 days.

(21) Appl. No.: 15/067,613

(22) Filed: Mar. 11, 2016

(65) Prior Publication Data

US 2016/0199453 A1 Jul. 14, 2016

Related U.S. Application Data

(63) Continuation of application No. PCT/US2015/000302, filed on Dec. 23, 2015.

(60) Provisional application No. 62/096,128, filed on Dec. 23, 2014.

(51) Int. Cl.

| | | |
|---|---|---|
| *A61K 38/28* | (2006.01) |
| *A61K 47/10* | (2017.01) |
| *A61K 9/00* | (2006.01) |
| *A61K 47/22* | (2006.01) |
| *A61K 45/06* | (2006.01) |
| *A61K 8/34* | (2006.01) |
| *A61K 8/36* | (2006.01) |
| *A61K 8/39* | (2006.01) |
| *A61K 8/49* | (2006.01) |
| *A61Q 19/00* | (2006.01) |

(52) U.S. Cl.
CPC ............... *A61K 38/28* (2013.01); *A61K 8/34* (2013.01); *A61K 8/361* (2013.01); *A61K 8/39* (2013.01); *A61K 8/4913* (2013.01); *A61K 9/0014* (2013.01); *A61K 45/06* (2013.01); *A61K 47/10* (2013.01); *A61K 47/22* (2013.01); *A61Q 19/007* (2013.01)

(58) Field of Classification Search
CPC .. A61K 31/192; A61K 9/4866; A61K 31/195; A61K 9/0014; A61K 47/10; Y10S 514/946; Y10S 514/947
See application file for complete search history.

(56) References Cited

U.S. PATENT DOCUMENTS

| | | | |
|---|---|---|---|
| 2004/0121023 A1* | 6/2004 | Stevens | A61K 31/047 424/616 |
| 2005/0002974 A1* | 1/2005 | Filbry | A61K 8/34 424/401 |
| 2007/0248658 A1* | 10/2007 | Zurdo Schroeder | A61K 8/0208 424/449 |
| 2009/0069364 A1* | 3/2009 | Carrara | A61K 9/0014 514/284 |
| 2009/0074844 A1* | 3/2009 | Nishiura | A61K 9/0014 424/449 |
| 2015/0272666 A1 | 10/2015 | Wang | |
| 2016/0136278 A1 | 5/2016 | Masuda et al. | |

FOREIGN PATENT DOCUMENTS

| | | |
|---|---|---|
| CN | 101045041 | 10/2007 |
| WO | WO 2013/109610 | 7/2013 |

OTHER PUBLICATIONS

International Patent Application No. PCT/US2015/000302: International Search Report and Written Opinion dated Mar. 31, 2016, 10 pages.
Trommer, H. et al. "Overcoming the Stratum Corneum: The Modulation of Skin Penetration" Skin Pharmacol Physiol May 2006; 19: pp. 106-121.

* cited by examiner

*Primary Examiner* — Mark V Stevens
(74) *Attorney, Agent, or Firm* — Baker & Hostetler LLP

(57) ABSTRACT

The present disclosure is directed to transdermal and moisturizing compositions.

7 Claims, No Drawings

TRANSDERMAL FORMULATIONS

CROSS REFERENCE TO RELATED APPLICATIONS

This application is a continuation of International Application No. PCT/US2015/000302, filed Dec. 23, 2015, which claims the benefit of U.S. Provisional Application No. 62/096,148, filed Dec. 23, 2014, the entireties of which are incorporated by reference herein.

BACKGROUND

Transdermal administration of therapeutic agents has many advantages, including convenience and gastrointestinal tract metabolism avoidance. But in the absence of penetration enhancing agents, many therapeutic agents are not capable of penetrating the skin in therapeutically effective concentrations. As such, compositions that facilitate the penetration of therapeutic agents through the skin are needed.

Also, the loss of skin moisture results in dry skin that can be uncomfortable, painful, or unattractive. Compositions that ameliorate dry skin and increase or maintain skin hydration are also needed.

SUMMARY

The present disclosure is directed to compositions comprising a first component, a second component, a $C_{2-10}$alkyl alcohol, and an organic acid having 1 to 25 carbon atoms, wherein the first and second components are further defined herein. Methods of making and using these compositions are also described.

DETAILED DESCRIPTION OF ILLUSTRATIVE EMBODIMENTS

The present disclosure may be understood more readily by reference to the following detailed description of desired embodiments and the examples included therein. In the following specification and the claims that follow, reference will be made to a number of terms which have the following meanings.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, "alkyl" refers to straight chain and branched chains having the indicated number of carbon atoms, usually from 1 to 20 carbon atoms, for example 1 to 8 carbon atoms, such as 1 to 6 or 1 to 7 carbon atoms. For example $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like.

As used herein, "alkenyl" refers to an unsaturated branched or straight-chain alkyl group having at least one carbon-carbon double bond. The group may be in either the cis or trans configuration about the double bond(s). The group may also be an aromatic group, for example, a phenyl or phenylene moiety. Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; phenylene, and the like. In certain embodiments, an alkenyl group has from 2 to 20 carbon atoms.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms.

The present disclosure is directed to compositions that moisturize the skin or that facilitate and/or enhance the transdermal permeation of therapeutic agents through the skin. As used herein, "moisturize" refers to increasing hydration or preventing further hydration loss. As used herein, the term "transdermal permeation" includes both percutaneous delivery and transmucosal delivery, that is, passage through skin or mucosal tissue and into the bloodstream. As used herein in reference to transdermal penetration, the term "enhancing" refers to increasing the rate at which a therapeutic agent penetrates the skin or mucosal tissue and enters the bloodstream. These compositions include a first component, a second component, an alcohol, an organic acid, and, optionally, water. Other compositions of the disclosure further comprise a therapeutic agent.

According to the disclosure, the first component comprises
a compound of formula I $$R-(OCH_2CH_2)_y-OH \quad (I)$$

wherein R is $C_{1-20}$alkyl, $C_{2-20}$alkenyl; or $C_{2-20}$alkynyl; and y is 1 to 25;
a tetrafunctional block copolymer surfactant terminating in primary hydroxyl groups;
a sorbitan derivative;
a $C_{8-10}$alkyl ammonium salt;
a compound of formula II $$HO-(CH_2CH_2O)_m-C(CH_3)(C_4H_9)-C\equiv C-C(CH_3)(C_4H_9)-(OCH_2CH_2)-OH \quad (II)$$

wherein m and n are each independently 1 to 25;
or a combination thereof.

In preferred embodiments of the disclosure, the first component is a compound of formula I. In some embodiments, R is $C_{1-20}$alkyl, which can either be a straight chain or branched alkyl. Preferred compounds of formula I wherein R is $C_{1-20}$alkyl include, for example, is cetomacrogol 1000; octadecan-1-ol, ethoxylated; polyoxyethylene (12)tridecyl ether; polyoxyethylene(10)tridecyl ether; fatty alcohol polyoxyethylene ether, polyoxyethylene branched nonylcyclohexyl ether (TRITON N-101), nonaethylene glycol monododecyl ether, 23-{[4-(2,4,4-trimethyl-2-pentanyl)cyclohexyl]oxy}-3,6,9,12,15,18,21-heptaoxatricosan-1-ol, and combinations thereof. Nonaethylene glycol monododecyl ether is particularly preferred.

In other embodiments, R is $C_{2-20}$alkenyl, which can either be a straight chain or branched alkenyl. Preferred compounds of formula I wherein R is $C_{2-20}$alkenyl include, for example, polyoxyl(10)oleyl ether, polyethylene glycol tert-octylphenyl ether (TRITON X-100), and combinations thereof.

In yet other embodiment, R is $C_{2-20}$alkynyl, which can either be a straight chain or branch alkynyl.

In those embodiments wherein the first component is a compound of formula I, y is 1 to 25. In preferred embodiments, y is 5 to 15, preferably 8 to 10, with 9 being particularly preferred. In other embodiments, y is 1, 2, 3, 4, 5, 6, 7, 8, 9, 10, 11, 12, 13, 14, 15, 16, 17, 18, 19, 20, 21, 22, 23, 24, or 25.

In other aspects of the disclosure, the first component is a tetrafunctional block copolymer surfactant terminating in primary hydroxyl groups. Such compounds are commercially available under the tradename TETRONIC and include ethylenediaminetetrakis(ethoxylate-Block-propoxylate).

In other embodiments of the discosure, the first component is a sorbitan derivative, for example, polyoxyethylene sorbitan tetraoleate, 1,4-anhydro-6-O-palmitoyl-D-glucitol (sorbitan, monohexadecanoate), a polyethylene glycol sorbitan monolaurate (e.g., TWEEN 20, TWEEN 40, TWEEN 60, TWEEN 85), and combinations thereof.

In still other embodiments of the disclosure, the first component is a $C_{8-10}$alkyl ammonium salt, for example, methyltrialkyl($C_8$-$C_{10}$)ammonium chloride (ADOGEN 464).

In other embodiments, the first component is a compound of formula II.

The compositions of the disclosure can comprise from about 0.1 vol. % to about 40 vol. % of the first component. In preferred embodiments, the compositions comprise from about 1 vol. % to about 40 vol. % of the first component. In other embodiments, the compositions comprise from about 0.1 vol. % to about 5 vol. % of the first component. For example, the compositions can comprise about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or about 40 vol. % of the first component.

According to the disclosure, the compositions also include a second component that comprises
an compound of the formula III $$R^2-N(R^1)-C(O)-R^3 \quad (III)$$

wherein
each $R^1$ is independently H or $C_{1-3}$alkyl; and
$R^2$ and $R^3$ are independently $C_{1-7}$alkyl or together with the atoms to which they are attached, form a lactam having 3 to 10 carbon atoms,
a sulfoxide;
a urea;
ethyl acetate;
or a combination thereof In preferred embodiments, the second component is compound of formula III. In some embodiments, $R^1$ is H. In other embodiments, $R^1$ is methyl, ethyl, propyl, or isopropyl, with methyl being particularly preferred.

In those embodiments wherein $R^2$ and $R^3$ are independently $C_{1-7}$alkyl, each of $R^2$ and $R^3$ is independently methyl, ethyl, propyl, isopropyl, butyl, s-butyl, t-butyl, pentyl, hexyl, or heptyl.

Preferably, $R^2$ and $R^3$, together with the atoms to which they are attached, form a lactam having 3 to 10 carbon atoms. For example, the lactam can include 3, 4, 5, 6, 7, 8, 9, or 10 carbons, which can be a part of the lactam ring or which can form exocyclic branching. Examples of preferred lactams include pyrrolidones such as 2-pyrrolidone, 1-methyl-2-pyrrolidone, 5-methyl-2-pyrrolidone, and 1-ethyl-2-pyrrolidone. Preferably, the lactam is 1-methyl-2-pyrrolidinone or 2-pyrrolidone.

In some embodiments, the second component is a sulfoxide, for example, dimethyl sulfoxide.

In other embodiments, the second component is a urea, for example an imidazolidinone.

The compositions of the disclosure can comprise from about 0.01 vol. % to about 10 vol. % of the second component. In preferred embodiments, the compositions comprise from about 0.01 vol. % to about 5 vol. % of the second component. In other embodiments, the compositions comprise from about 0.01 vol. % to about 4 vol. % of the second component. For example, the compositions can comprise about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or about 10 vol. % of the second component.

In some embodiments of the disclosure, the ratio, by volume, of the first component to the second component is about 10:1 to about 4:1.

Alcohols for use in the compositions of the disclosure include $C_{2-10}$alkyl alcohols having at least one —OH moiety or at least two —OH moieties. For example, preferred alcohols include glycerol, propylene glycol, ethanol, isopropanol, 1-propanol, butanol, t-butanol, pentanol, 1-octanol, and combinations thereof, with ethanol being particularly preferred.

The compositions of the disclosure can comprise from about 0.1 vol. % to about 50 vol. % of the $C_{2-10}$ alkyl alcohol. In preferred embodiments, the compositions comprise from about 1 vol. % to about 50 vol. % of the $C_{2-10}$ alkyl alcohol. In other embodiments, the compositions comprise from about 0.1 vol. % to about 5 vol. % of the $C_{2-10}$ alkyl alcohol. For example, the compositions can comprise about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 vol. % of the $C_{2-10}$ alkyl alcohol.

The compositions of the disclosure also include an organic acid having 1 to 25 carbon atoms. For example, organic acids for use in the disclose compositions include acetic acid, ascorbic acid, lactic acid, glycolic acid, propionic acid, and combinations thereof Other organic acids for use in the disclosure include fatty acids. As used herein, the term "fatty acid" has its ordinary meaning as would be understood by a person of ordinary skill in the art and includes a molecule having a carboxylic group and a hydrocarbon chain. Descriptions of the number of carbon atoms in a fatty acid herein refer to the number of carbon atoms in the hydrocarbon chain of the fatty acid, irrespective of whether the hydrocarbon chain is straight or branched.

As used herein, the term "fatty acid" includes saturated fatty acids, which do not contain any double or triple bonds in the hydrocarbon chain. Saturated fatty acids include, but are not limited to propionic acid (C3) (by way of example, C3 indicates propionic acid has 3 carbon atoms in its hydrocarbon chain; the number of carbon atoms in the hydrocarbon chain of other example fatty acids is denoted in analogous fashion herein), butyric acid (C4), valeric acid (C5), caproic acid (C6), enanthic acid (C7), caprylic acid (C8), pelargonic acid (C9), capric acid (C10), undecylic acid (C11), lauric acid (C12), tridecylic acid (C13), myristic acid (C14), pentadecylic acid (C15), palmitic acid (C16), margaric acid (C17), stearic acid (C18), isostearic acid (C18), nonadecylic acid (C19), arachidic acid (C20), heneicosylic acid (C21), behenic acid (C22), tricosylic acid (C23), lignoceric acid (C24), pentacosylic acid (C25), cerotic acid (C26), heptacosylic acid (C27), montanic acid (C28), nonacocylic acid (C29), melissic acid (C30), henatriacontylic acid (C31), lacceroic acid (C32), psyllic acid (C33), geddic acid (C34), ceroplastic acid (C35) and hexatriacontylic acid (C36).

As used herein, the term "fatty acid" also includes monounsaturated fatty acids, which contain one double or triple bond in the hydrocarbon chain, and polyunsaturated fatty acids, which contain more than one double and/or triple bond in the hydrocarbon chain. Such acids include, but are not limited to the omega 3, omega 6, omega 9 fatty acids, other fatty acids such as myristoleic and palmitoleic acid and conjugated fatty acids. Examples of monounsaturated and polyunsaturated fatty acids include but are not limited to, (a) omega 3 fatty acids, such as hexadecatrienoic acid (C16:3); (by way of example, C16:3 indicates hexadecatrienoic acid has 16 carbon atoms in its hydrocarbon chain and 3 double bonds; the number of carbon atoms and double bonds in the hydrocarbon chain of other example unsaturated fatty acids is denoted in analogous fashion herein), alpha linolenic acid (C18:3) and eicosapentanoic acid (20:5), (b) omega 6 fatty acids, such as linoleic acid (18:2), docosadienoic acid (C22: 2), arachidonic acid (C20:4) and tetracosatetraenoic acid (C24:5), (c) omega 9 fatty acids, such as oleic acid (C18:1), eicosenoic acid (C20:1) and nevronic acid (C24:1), and (d) conjugated fatty acids such as rumenic acid (C18:2), eleostatic acid (C18:3), and rumelenic acid (C18:3).

As used herein, the term "fatty acid" also includes branched fatty acids. Examples of branched fatty acids include, but are not limited to, monomethyl branched fatty acids, such as 14-methyl pentadecanoic acid, 6-methyl caprylic acid, 4-methyl-3-pentenoic acid, (pyroterebic acid), 2-methyl-2E-butenoic acid (tiglic acid), 2-methyl-2Z-butenoic acid (angelic acid), multimethyl branched acids, isoprenoid fatty acids (vittatalactone, all-trans-retinoic acid), branched methoxy fatty acids and hydroxy and other fatty acids such as 2-hydroxyoctanoic acid and 4-oxopentanoic acid.

The compositions of the disclosure can comprise from about 0.01 vol. % to about 15 vol. % of the organic acid. In some embodiment, the compositions comprise from about 1 vol % to about 15 vol % of the organic acid. In preferred embodiments, the compositions comprise from about 0.01 vol. % to about 5 vol. % of the organic acid. In other embodiments, the compositions comprise from about 0.01 vol. % to about 3 vol. % of the organic acid. For example, the compositions can comprise about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 vol. % of the organic acid.

Compositions of the disclosure can be anhydrous. As used herein, "anhydrous" refers to compositions comprising less than 1 vol. % of water, preferably less than 0.05 vol. % or less than 0.025 vol. % of water. Methods of determining water content are known in the art.

Compositions of the disclosure can include water. In some embodiments, the compositions can comprise up to 99 vol. % of water. In still other aspects, the compositions can comprise 5, 10, 20, 30, 40, 50, 60, 70, 80, 90, 95, or 99 vol. % of water. In other embodiments, the compositions can comprise 90, 91, 92, 93, 94, 95, 96, 97, 98, or 99 vol. % of water.

Compositions of the disclosure that include water can optionally contain one or more physiologically acceptable salts. While not being bound by any particular theory, it is believed that controlling the amount of salt that is present allows one to control the depth to which the present composition penetrate skin, with the concentration of salt having a generally inverse relationship to the penetration depth. Salts for use in the compositions include, but are not limited to, sodium chloride, potassium chloride, and mixtures thereof. A preferred form of sodium chloride is bacteriostatic sodium chloride solution.

The compositions of the disclosure can also include a therapeutic agent. As used herein, the term "therapeutic agent" refers to a compound that, upon administration to a patient in a therapeutically effective amount, provides a therapeutic benefit to the patient. A therapeutic agent may be referred to herein as a drug or biologic. Those skilled in the art will appreciate that the term "therapeutic agent" is not limited to drugs or biologics, or to materials that have received regulatory approval.

For example, such therapeutic agents include, but are not limited to, hormones such as estrogens, progestins, and androgens for both male and female health, adrenocortical steroids and their synthetic analogs for inflammation and/or various manifestations of adrenal insufficiency or pituitary hormone excess, antinausea/antiemetic drugs, tricyclic antidepressants, migraine and other pain drugs including NSAIDs and narcotics, hypnotics, some beta blockers, alpha blockers, neuromuscular blocking agents, diuretics, antimalarial drugs, dermatologicals, antimetabolites, peptides such as leuprolide, goserelin or histrelin. In other embodiments the therapeutic agent may be, but is not limited to, an agent to treat Alzheimer's, an anabolic agent, an analgesic agent, an anesthetic agent, an antacid, an anti-asthmatic agent, an anticholesterolemic agent, an anti-lipid agent, an anti-coagulant, an anti-convulsant, an anti-diarrheal, an antiemetic, an anti-inflammatory agent, an antifungal agent, an anti-manic agent, an anti-migraine, an anti-nauseant, a CNS anti-depressant, an antineoplastic agent, an anti-obesity agent, an anti-Parkinson's agent, an anti-pyretic agent, an anti-spasmodic agent, an anti-thrombotic agent, an anti-uricemic agent, an anti-anginal agent, an antihistamine, an anti-tussive, an appetite suppressant, a biological, a cerebral dilator, a central nervous system agent, a coronary dilator, a decongestant, a diuretic, an erythropoietic agent, an expectorant, a gastrointestinal sedative, a hormone or hormone agonist or antagonist, an agent possessing mixed agonist and antagonist properties on a hormone receptor, a hyperglycemic agent, a hypoglycemic agent, a prostaglandin or prostanoid, an estrogen or anti-estrogen, a progestogen or anti-progestin, an androgen or anti-androgen, an opiate or opioid agonist or antagonist, a phenothiazine, a butyrophenone, a benzamide, a glucocorticoid, a dopamine antagonist, a hypnotic, a hypoglycemic agent, an ion exchange resin, a laxative, a mineral supplement, a mucolytic agent, a neuromuscular drug, an NSAID, an oligonucleotide, an anti-Parkinson's agent, a peptide or polypeptide, a peripheral vasodilator, a psychotropic, a polynucleotide, a sedative, a stimulant, a thyroid agent, an anti-thyroid agent, a uterine relaxant, a cervical ripening agent, an agent for the induction of labor, a vitamin, a prodrug, or an agent that promotes healing.

Therapeutics also include benzoyl peroxide, salicylic acid, iodine, and oregano oil.

Specific examples of therapeutic agents suitable for use in compositions of the invention include ropinirole, pramipexole, sumatriptan, zolmitriptan, rizatriptan, almotriptan, eletriptan, naratriptan, frovatriptan, zolpidem, zaleplon, eszopiclone, ramelteon, doxepin, ketoprofen, ketorolac, piroxicam, meloxicam, diclofenac, mifepristone, ulipristal, sildenafil, vardenafil, tadalafil, alprostadil, letrozole, anastrozole, oxycodone, hydrocodone, buprenorphine, fentanyl, sufentanyl, alfentanyl, morphine, naloxone, naltrexone, leuprolide, goserelin, histrelin, pyridoxine, doxylamine, dimenhydronate, diphenhydramine, meclizine, promethazine, prochlorperazine, droperidol, metaclopramide, haloperidol, prednisone, methylprednisolone, cortisol, thyrotropin, thyrotropin-releasing hormone, estradiol, progesterone, gonadotropin-releasing hormone, gonadotropin-releasing hormone agonists or antagonists, and insulin.

Additional compounds suitable for use in compositions of the invention include estrogens , which can be useful as contraceptives and/or hormone therapies for menopause and other endocrine conditions. Suitable estrogens not mentioned elsewhere in this specification include ethinyl estradiol and estradiol-17beta.

Additional compounds suitable for use in compositions of the invention include progesterones and progestins, which can useful as contraceptives, hormone therapies, or both, for menopause and other endocrine conditions. Suitable progesterones and progestins not mentioned elsewhere in this specification include: Progesterone, Norgestimate, Norelgestromin (also called 17-deacetyl norgestimate), Norgestrel, Levo-norgestrel, Cyproterone Acetate, Gestodene, Desogestrel, Dienogest, Drosperinone, Norethindrone, and Norethindrone acetate.

Other compounds suitable for use in compositions of the invention include anti-infectives. Suitable anti-infectives not mentioned elsewhere in this specification include Fenticonazole (base, nitrate or both) and Fluconazole.

Additional compounds suitable for use in compositions of the invention include nutritional supplements and vitamins. Suitable nutritional supplements and vitamins not mentioned elsewhere in this specification include Calcium Carbonate, Cholecalciferol (a metabolite of Vitamin D), Folic Acid, Folate, and Metafolin.

Other compounds suitable for use in compositions of the invention include compounds useful for treating central nervous system (CNS) disorders. Suitable compounds useful for treating central nervous system (CNS) disorders not mentioned elsewhere in this specification include Methylphenidate (e.g., for ADHD), Paroxetine (base, mesylate salt, or both), Valproic Acid, Lithium carbonate, Fentanyl, Lidocaine, and Rivastigmine.

In preferred embodiments, a composition of the invention includes a therapeutic agent that is a serotonin receptor antagonist. Preferably, the serotonin receptor antagonist comprises a 5-HT$_3$ receptor antagonist. Even more preferably, the serotonin receptor antagonist is selected from ondansetron, dolasetron, granisetron, tropisetron, palonosetron, or salts thereof.

Compositions of the invention may be designed to be administered to the skin or mucosal tissue of a patient in need of treatment. Compositions of the invention may be formulated as gels, transdermal patches, lotions, creams, sprays, mists, emulsions, or dispersions. Appropriate excipients for formulating a gel, transdermal patch, lotion, cream, spray, or mist are readily apparent to a person of skill in the art and include, but are not limited to, stabilizers, emulsifiers, thickeners, antimicrobials, humectants, propellants, spreading agents, polymers, and adhesives, such as pressure sensitive adhesives. In particular, excipients that may be used to form a transdermal gel include, but are not limited to, alcohols, glycols, glycerin, butylated hydroxytoluene (BHT), and water.

Also within the scope of the disclosure are methods comprising administering any of the described compositions to the skin of a mammal for a time and under conditions effective to achieve passage of at least a portion of the composition through the skin. Skin permeation can be measured using techniques known in the art.

The compositions of the disclosure can be used to administer a therapeutic agent to a mammal. For example, in preferred embodiments, these methods comprise applying any of the described compositions to the skin of a mammal for a time sufficient to achieve permeation of at least a portion of the therapeutic agent through the skin. Therapeutic agent skin permeation can be measured using techniques known in the art.

The compositions of the disclosure can be used in methods of moisturizing the skin. For example, these methods can comprising identifying on a mammal an area of skin having an undesirably low level of moisture and applying any of the described compositions to the skin. Preferably, the level of moisture is increased or does not decrease.

The compositions described herein can be applied to any convenient skin surface. Skin surfaces of interest include, but are not limited to: arms, leg, torso, head, neck, etc. The surface area that is covered by the transdermal formulation following application is generally sufficient to provide for the desired amount of agent administration, and in certain embodiments ranges from about 1 cm² to about 200 cm².

The compositions described herein can be applied a single time or a plurality of times over a given time period, e.g., the course of the disease condition being treated, where the dosing schedule when a plurality of patches are administered over a given time period may be daily, weekly, biweekly, monthly, etc.

The compositions of the disclosure will, in some embodiments, include, in addition to the above-discussed components, one or more additional components. Additional components include, but are not limited to, a transdermal absorption enhancer, a preservative (e.g., paraben), an anti-oxidant, a stabilizing agent, a filling agent that contains a hydrophilic polymer; a cross-linking agents; and a plasticizing agent.

The following example is provided to illustrate the compositions, processes, and properties of the present disclosure. The example is merely illustrative and not intended to limit the disclosure to the materials, conditions, or process parameters set forth therein.

EXAMPLE

Example 1

Moisturizing Composition

Nonaethylene glycol monododecyl ether (3 mL, 5.14 vol %), 1-methyl-2-pyrrolidinone (0.3 mL, 0.515 vol. %), ethanol (4 mL, 6.86 vol. %), oleic acid (1 mL, 1.72 vol. %), and water (50 mL, 85.8 vol. %) are combined to form an admixture. The resulting composition is applied to an area of the skin that is dry or in need of moisture in order to alleviate symptoms of dry skin.

Example 2

Aqueous Composition for Transdermal Administration of a Therapeutic Agent

Nonaethylene glycol monododecyl ether (3 mL), 1-methyl-2-pyrrolidinone (0.3 mL), ethanol (4 mL), oleic acid (1 mL), and water (50 mL) are combined to form an admixture. An effective amount of a therapeutic agent is combined with the admixture to form a transdermal composition. The transdermal composition is applied to the skin of a patient in an amount and for a time sufficient for the therapeutic agent to permeate through the skin and into the patient's bloodstream to achieve a therapeutic effect.

Example 3

Anhydrous Composition for Transdermal Administration of a Therapeutic Agent

Nonaethylene glycol monododecyl ether (3 mL), 1-methyl-2-pyrrolidinone (0.3 mL), ethanol (4 mL), and linoleic acid (1 mL) are combined to form an admixture. An effective amount of a therapeutic agent is combined with the admixture to form a transdermal composition.

Example 4

Transdermal Administration of a Therapeutic Agent Using an Anhydrous Composition The transdermal composition of Example 3 is applied to the skin of a patient in an amount and for a time sufficient for the therapeutic agent to permeate through the skin and into the patient's bloodstream to achieve a therapeutic effect.

Example 5

Aqueous, Sensitive Tissue Transdermal Composition

The composition of Example 3 (1 mL) is mixed with 99 mL of water. The resulting aqueous composition can be applied to a sensitive tissue, for example a mucous membrane, for a time sufficient for the therapeutic agent to permeate through the sensitive tissue and into the patient's bloodstream to achieve a therapeutic effect.

Example 6

Aqueous, Normal Skin Transdermal Composition

The composition of Example 3 (1 mL) is mixed with water 49 mL of water. The resulting aqueous composition can be applied to normal skin for a time sufficient for the therapeutic agent to permeate through the skin and into the patient's bloodstream to achieve a therapeutic effect.

Example 7

Aqueous, Insulin Transdermal Composition

Nonaethylene glycol monododecyl ether (3 mL), 1-methyl-2-pyrrolidinone (0.3 mL), ethanol (4 mL), and linoleic acid (1 mL) are combined. Insulin (3 mL, 100 units/mL, LANTUS SOLOSTAR, Sanofi) is then added to form an admixture. The admixture (1 mL) is then combined with 24 mL of water. The resulting aqueous composition can be applied to skin or tissue for a time sufficient for the insulin to permeate through the skin or tissue and into the patient's bloodstream to achieve a therapeutic effect.

Example 8

Aqueous, Insulin Transdermal Composition

Nonaethylene glycol monododecyl ether (3 mL), 1-methyl-2-pyrrolidinone (0.3 mL), ethanol (4 mL), and linoleic acid (1 mL) are combined. Insulin (3 mL, 100 units/mL, LANTUS SOLOSTAR, Sanofi) is then added to form an admixture. The admixture (1 mL) is then combined with 32.3 mL of water. The resulting aqueous composition can be applied to skin or tissue for a time sufficient for the insulin to permeate through the skin or tissue and into the patient's bloodstream to achieve a therapeutic effect.

What is claimed:

1. A composition comprising
nonaethylene glycol monododecyl ether,
1-methyl-2-pyrrolidone,
ethanol,
linoleic acid, and
a therapeutic agent that is insulin,
wherein the composition allows for the transdermal delivery of the therapeutic agent.

2. The composition of claim 1, wherein the composition is anhydrous.

3. The composition of claim 1, further comprising water.

4. The composition of claim 1, wherein the ratio (v/v) of the nonaethylene glycol monododecyl ether to the 1-methyl-2-pyrrolidone is from 9:1 to 11:1.

5. The composition of claim 1, further comprising an antimicrobial agent.

6. The composition of claim 4, wherein the ratio (v/v) of the nonaethylene glycol monododecyl ether to the 1-methyl-2-pyrrolidone is 10:1.

7. A method comprising applying a composition of claim 1 to the skin or a mucous membrane of a mammal for a time sufficient to achieve permeation of at least a portion of the therapeutic agent through the skin or the mucous membrane.

* * * * *

UNITED STATES PATENT AND TRADEMARK OFFICE
CERTIFICATE OF CORRECTION

PATENT NO. : 9,687,528 B2
APPLICATION NO. : 15/067613
DATED : June 27, 2017
INVENTOR(S) : Steven Hoffman It is certified that error appears in the above-identified patent and that said Letters Patent is hereby corrected as shown below:

On the Title Page

Related U.S. Application Data:
Item (60) After "Provisional application No." delete "62/096,128," and insert -- 62/096,148, --.

Signed and Sealed this
Twenty-first Day of November, 2017

Joseph Matal
*Performing the Functions and Duties of the
Under Secretary of Commerce for Intellectual Property and
Director of the United States Patent and Trademark Office*